(12) United States Patent
Nakamura

(10) Patent No.: US 6,863,225 B2
(45) Date of Patent: *Mar. 8, 2005

(54) DEVICE AND METHOD FOR APPLYING ADHESIVE TO MATERIALS SUCH AS STRANDS

(75) Inventor: Yukio Nakamura, Tokyo (JP)

(73) Assignee: Nordson Corporation, Westlake, OH (US)

(*) Notice: Subject to any disclaimer, the term of this patent is extended or adjusted under 35 U.S.C. 154(b) by 598 days.

This patent is subject to a terminal disclaimer.

(21) Appl. No.: 09/805,085

(22) Filed: Mar. 13, 2001

(65) Prior Publication Data

US 2001/0022155 A1 Sep. 20, 2001

(30) Foreign Application Priority Data

Mar. 14, 2000 (JP) ........................................ 2000-117263

(51) Int. Cl.[7] ................................................ B05B 1/28
(52) U.S. Cl. .................... 239/105; 239/106; 239/296; 239/422; 239/423; 118/302; 118/313; 118/62
(58) Field of Search ................... 239/296, 297, 239/105, 106, 421, 422, 423; 118/302, 325, 313, 315, 62

(56) References Cited

U.S. PATENT DOCUMENTS

| | | | |
|---|---|---|---|
| 1,868,690 | A | 7/1932 | Brigham |
| 2,231,808 | A | 2/1941 | Isaac |
| 2,424,743 | A | 7/1947 | Davis |

(List continued on next page.)

FOREIGN PATENT DOCUMENTS

| | | |
|---|---|---|
| EP | 0235815 | 9/1987 |
| GB | 2148183 | 5/1985 |
| JP | 11244774 A | 9/1999 |

OTHER PUBLICATIONS

Syang–Peng Rwei, *Dog–Legging in the Melt Spinning Process,* Polymer Engineering and Science, vol. 38, No. 2, pp. 341–347, Feb. 1998.
J&M Laboratories, *Durastitch™ Technology,* New Product Release Manual, Feb. 1997.
Rajiv S. Rao et al., *Vibration and Stability in the Melt Blowing Process,* Ind. Eng. Chem., 32, pp. 3100–3111, 1993.
Nordson Corporation, *Recouping the Costs of Disposable Diaper Improvements,* Brochure, Jan. 1989.
Exxon Chemical Company, *Meltblowing Process,* Brochure, Sep. 1994.
Nordson Corporation, *Adhesive and Powder Application Systems for the Nonwovens Industry,* Brochure, 1992.
Synthetic Surfaces Inc., *Roll WIth It: Aqueous Adhesives Bond Rubber Covered Rollers,* Adhesive Age, Feb. 1994.
J and M Laboratories, Inc., *DuraSystem Holt Melt Applicators,* Brochure, undated.
Nordson Corporation, *Trends: Stranded Plastic Solutions,* Brochure, undated.

Primary Examiner—Dinh Q. Nguyen
(74) Attorney, Agent, or Firm—Wood, Herron & Evans, L.L.P.

(57) ABSTRACT

A device and method for applying adhesive to materials, such as elastic strands, used in the production of nonwoven products. Generally, a nozzle is provided and includes a liquid discharge orifice configured to discharge a bead of liquid adhesive. First and second pattern air discharge orifices are associated with the first liquid discharge orifice to vacillate or oscillate the adhesive bead. First and second cleaning and stabilizing air discharge orifices are also associated with the first liquid discharge orifice. These latter air discharge orifices keep airborne contaminants away from the associated liquid discharge orifice and also stabilize the oscillation of the adhesive bead in a single plane. A method in accordance with the invention includes using the nozzle to dispense a vacillating bead of adhesive onto a strand of material.

12 Claims, 4 Drawing Sheets

U.S. PATENT DOCUMENTS

| | | |
|---|---|---|
| 3,459,615 A | 8/1969 | Eilerman |
| 3,543,332 A | 12/1970 | Wagner et al. |
| 3,615,995 A | 10/1971 | Buntin et al. |
| 3,762,982 A | 10/1973 | Whittington |
| 3,849,040 A | 11/1974 | McGinnis et al. |
| 3,903,840 A | 9/1975 | Gemelli |
| 4,031,854 A | 6/1977 | Sprague, Jr. |
| 4,098,632 A | 7/1978 | Sprague, Jr. |
| 4,135,903 A | 1/1979 | Ohsato et al. |
| 4,147,580 A | 4/1979 | Buell |
| 4,185,981 A | 1/1980 | Ohsato et al. |
| 4,259,220 A | 3/1981 | Bunnelle et al. |
| 4,379,016 A | 4/1983 | Stemmler et al. |
| 4,418,123 A | 11/1983 | Bunnelle et al. |
| 4,473,986 A | 10/1984 | Zeigler |
| 4,525,229 A | 6/1985 | Suzuki et al. |
| 4,543,099 A | 9/1985 | Bunnelle et al. |
| 4,626,305 A | 12/1986 | Suzuki et al. |
| 4,666,542 A | 5/1987 | De Jonckheere |
| 4,687,477 A | 8/1987 | Suzuki et al. |
| 4,695,278 A | 9/1987 | Lawson |
| 4,710,187 A | 12/1987 | Boland et al. |
| 4,719,261 A | 1/1988 | Bunnelle et al. |
| 4,762,521 A | 8/1988 | Roessler et al. |
| 4,762,582 A | 8/1988 | de Jonckheere |
| 4,770,656 A | 9/1988 | Proxmire et al. |
| 4,788,089 A | 11/1988 | Skipper |
| 4,798,603 A | 1/1989 | Meyer et al. |
| 4,842,666 A | 6/1989 | Werenicz |
| 4,844,003 A | 7/1989 | Slautterback et al. |
| 4,880,420 A | 11/1989 | Pomparelli |
| 4,891,249 A | 1/1990 | McIntyre |
| 4,900,384 A | 2/1990 | Sanders et al. |
| 4,917,696 A | 4/1990 | De Jonckheere |
| 4,949,668 A | 8/1990 | Heindel et al. |
| 4,960,619 A | 10/1990 | Slautterback et al. |
| 4,982,688 A | 1/1991 | Rothen |
| 5,024,667 A | 6/1991 | Malcolm et al. |
| 5,026,450 A | 6/1991 | Cucuzza et al. |
| 5,057,571 A | 10/1991 | Malcolm et al. |
| 5,102,484 A | 4/1992 | Allen et al. |
| 5,171,512 A | 12/1992 | Mende et al. |
| 5,208,064 A | 5/1993 | Becker et al. |
| 5,217,553 A | 6/1993 | Marx et al. |
| 5,275,676 A | 1/1994 | Rooyakkers et al. |
| 5,342,647 A * | 8/1994 | Heindel et al. ............. 427/2.31 |
| 5,501,756 A | 3/1996 | Rollins et al. |
| 5,507,909 A | 4/1996 | Rollins et al. |
| 5,525,175 A | 6/1996 | Blenke et al. |
| 5,577,306 A | 11/1996 | Gold |
| 5,882,573 A | 3/1999 | Kwok et al. |
| 5,902,540 A | 5/1999 | Kwok |
| 5,904,298 A | 5/1999 | Kwok et al. |
| 6,074,597 A | 6/2000 | Kwok et al. |
| 6,077,375 A * | 6/2000 | Kwok ........................ 156/161 |
| 6,197,406 B1 | 3/2001 | Kwok |
| 6,200,635 B1 | 3/2001 | Kwok |
| 6,378,782 B1 * | 4/2002 | Craine et al. ................ 239/270 |
| 6,719,846 B2 * | 4/2004 | Nakamura et al. ........... 118/313 |

\* cited by examiner

DEVICE AND METHOD FOR APPLYING ADHESIVE TO MATERIALS SUCH AS STRANDS This application claims the priority of Japanese Patent Application No. 2000-117263 filed Mar. 14, 2000, the disclosure of which is hereby fully incorporated by reference herein.

FIELD OF THE INVENTION

The present invention pertains to a device and a method for applying an adhesive to materials such as strands, which are used by subsequently bonding them to a substrate.

BACKGROUND OF THE INVENTION

The structure of a disposable diaper is disclosed, for example, in Japanese Patent Kokai No. 11[1999]-285,510. In the structure of this disposable diaper an elastic strand(s) is provided at various locations including at the bending section and free ends of a sheet so as to form a barrier. In the process of producing disposable diapers with this kind of structure, the disposable diapers are produced through steps such as applying an adhesive to elastic strand material being fed continuously, then bonding the elastic strand material to a base or substrate material which forms the main part of the diaper and which is also fed continuously, and finally in a subsequent step cutting the resulting product into individual diapers.

Not only in the production of the aforesaid disposable diapers but also in the process of producing, for example, disposable surgical gowns to be used in operating rooms, elastic strand material and nonwoven or woven fabrics are bonded together with an adhesive. Also, in a process of this kind, the materials to be coated with the adhesive are not always elastic members, there are cases where strand materials with no stretching properties are coated with the adhesive and bonded to a substrate. Accordingly, the term "strand material" or similar terms as used in the present specification are meant to also include both elastic materials such as elastic yarn and nonelastic material.

Furthermore, the cross-sectional shape of the strand material is not only circular but includes various shapes such as elliptic, square, and rectangular, and the thickness also ranges from the order of hundredths of a millimeter to the order of several millimeters. Thus, there are no particular limitations with regard to the shape and thickness of the strand material. As the adhesive to be used, a hot-melt adhesive is used in many cases, but other types of adhesive can be used as well.

A conventional device and method for applying an adhesive to strand material in the process of producing the aforesaid disposable diapers or other products will now be explained with reference to FIGS. 9–12. FIG. 9 shows a front view of the conventional coating device. FIG. 10 shows a vertical sectional view of the conventional coating device. FIG. 11 shows an expanded view of the leading end portion of FIG. 10. FIG. 12 shows an enlarged view of encircled portion D of FIG. 9.

In FIGS. 9–12, coating device 51 includes a valve mechanism 65 which is opened and closed by operating air 80. A gun body 52 forms the coating device 51; a cylinder block 53 is attached with a plurality of bolts 54 to the top of the gun body 52, and a piston 55 moves up and down and is located inside the cylinder block 53. A valve stem 56 is fastened to the piston 55 and is extended into a liquid chamber 59 through a seal block 57. A seal member 58 is provided in the gun body 52, and includes a valve ball 60 at the leading end.

Furthermore, a valve seat member 62 that has an outlet 62a is attached with a plurality of bolts 63 to the lower part of the gun body 52. A screw 62b is provided in the lower outer diameter section of the valve seat member 62. The valve ball 60 is at the leading end of the valve stem 56 and the valve seat member 62 forms the valve mechanism 65. A spring 75 is placed between the large-diameter section at the leading end of the valve stem 56 and the underside of the seal block 57, and closes the valve mechanism 65 by forcing the valve stem 56 downward at all times.

A nozzle member 66 has a flange section 66a. A cap nut 67 is provided with a small-diameter section 67a to be engaged with the flange section 66a of the nozzle member 62 and a screw section 67b to be engaged with the screw 62b of the valve seat member 62. The nozzle member 66 is attached to the lower end of the valve seat member 62 by engaging the small-diameter section 67a of the cap nut 67 with the flange section 66a, and attaching the screw section 67b of the cap nut 67 over the screw 62b.

Moreover, a flat section 66b is formed in the nozzle member 66, and a nozzle plate 68 is fastened with a plurality of bolts 69 to the flat section 66b. A through-hole 66c communicates with the outlet 62 of the valve seat member 62. A horizontally long groove 66d extends in the horizontal direction in communication with the through-hole 66c and opens to the flat section 66b, and three branched nozzle grooves 66e communicate with the horizontal groove 66d in the nozzle member 66. The horizontal groove 66d and the nozzle grooves 66e are combined in such a way that the nozzle plate 68 covers the open section of the grooves. The nozzle groove 66e is open at the lower end and a nozzle hole 70 couples with the nozzle plate 68.

The lower ends of the nozzle member 66 and the nozzle plate 68 have exactly the same shape, and are formed like teeth of a comb stretching to below the nozzle hole 70. An inverted V-shape groove 61 with its lower end slightly spreading is formed with the nozzle hole 70 at the center. This groove 61 plays a role as a guide for the strand material 14 to be coated with the adhesive. An example of the conventional coating device shown in the figures is a device wherein three nozzle holes 70 are formed so as to apply three strands 14 simultaneously by one coating device 51. The device is not limited to this and may have one nozzle hole or many more nozzle holes to enable the coating of one or more strands.

To return to the explanation of the gun body 52, the gun body 52 is provided with an air through-hole 52a for feeding operating air 80 to the underside of the piston 55, and an adhesive through-hole 52b for feeding an adhesive 81 to the liquid chamber 59. The gun body 52 is fastened with a plurality of bolts 72 to a manifold 71. The manifold 71 is provided with an air feed hole 71a that communicates with the air through-hole 52a of the gun body 52, and an adhesive feed hole 71b that communicates with the adhesive through-hole 52b. An operating air feed device 73 is connected with the air feed hole 71a of the manifold 71 via a tubular path such as a hose, and an adhesive feed device 74 is connected with the adhesive feed hole 71b of the manifold 71 via a tubular path such as a hose.

In the coating device thus constructed, the adhesive 81 fed from the adhesive feed device 74 is stored in the liquid chamber 59 through the adhesive feed hole 71b of the manifold 71 and the adhesive through-hole 52 of the gun body 52. If operating air 80 is fed from the operating air feed device 73 to the underside of the piston 55, the piston 55 and valve stem 56 operate upward against the force of the spring 75, and the valve mechanism 65 is opened.

While the valve mechanism 65 is open, the adhesive 81 in the liquid chamber 59 is extruded from the nozzle hole 70 via through-hole 66c of the nozzle member 66 and the horizontally long groove 66d from the outlet 62a of the valve seat member 62, and applied to the surface of strand material 14. In this case, the nozzle hole 70, the topmost part of the inverted V-shape grooves 61 of the nozzle member 66 and nozzle plate 68 are in contact with the strand material 14. The strand material 14 is coated with the adhesive 81 and adhered to the substrate in a not-illustrated device in a later step. If the feeding of operating air 80 is stopped and the air pressure on the underside of the piston 55 is released, the valve mechanism 65 closes by the force of the spring 75, and the extrusion of adhesive 81 from the nozzle hole 70 stops. The adhesive can be applied intermittently by the opening and closing operations of the valve mechanism 65.

In another known device, the adhesive is dispensed in a spiral pattern towards the strand material. One or multiple strands can be used and the adhesive can be dispensed from one or multiple nozzles. The spiral pattern of adhesive wraps completely around the strand material while the strand material is still separate from the substrate. The operating characteristics of this system such as adhesive pressure, air pressure, distance from the dispenser nozzle to the strand material can all be varied to control the extent of the wrap around and to control the amount of adhesive captured by the strand material. It is well known to those of ordinary skill in the field that the strand material can capture substantially all of the spiral adhesive or some portion of the spiral adhesive can pass by the strand material to contact the substrate. This known device is described in U.S. Pat. No. 4,842,666 and as shown in "Adhesive and Powder Application Systems for the Nonwoven Industry", Nordson Corporation, October 1992, both of which are incorporated herein by reference.

The first aforementioned adhesive coating device is known to have the following problems. If the thickness or shape of the strand material changes, the size of the inverted V-shape groove also must be changed, and this leads to troublesome operation and extra time. Furthermore, since the strand material is coated with the adhesive in constant contact with the nozzle hole and inverted V-shape groove while being transferred at high speed (usually 70–400 m/minute), stress develops in the strand material. As a result, the strand material can be severed, or the grooves of the nozzle member can wear during lengthy operation and become larger than the diameter of the strand material. In some cases the adhesive drips from the strand material onto the substrate.

Furthermore, although the adhesive is applied sufficiently to the area facing the nozzle hole of the strand material, the adhesive is not applied sufficiently to the opposite underside, and this can result in poor adhesion. Moreover, because fiber products are being transferred at high speed, the operating environment is such that fine fibrous dust is more easily formed by friction between the fiber products and mechanical devices. This fine airborne dust adheres readily to the nozzle hole sections, and this adhered dust piles up over time, solidifies, and destabilizes the coating process. In an extreme case, the extrusion of the adhesive becomes obstructed and the strand material can be severed.

Yet another problem has been that, when applying the adhesive intermittently by controlling the opening and closing of the valve mechanism, the adhesive remaining downstream from the valve mechanism is inevitably drawn out by the strand material even after the valve mechanism is closed, and a poor final coating results.

In the second known device mentioned above, the spiral pattern is sometimes difficult to control across the length of the strand material. This can lead to uneven or nonuniform application of the spiral bead of adhesive to the strand material.

Thus, the invention of the present application was developed in view of the above-mentioned problems, and is aimed at providing a device and a method for applying an adhesive to material such as strand material, which requires no change in the device even if the thickness or shape of the strand material is changed, by installing the coating device in noncontact with the strand material. The present invention can achieve good all-around attachment of the adhesive, and moreover can carry out high-quality application of the adhesive with clean nozzles without any adhesion of dust and while maintaining a more uniform back and forth or vacillating adhesive bead pattern.

SUMMARY OF INVENTION

The present invention generally provides a nozzle for dispensing a liquid adhesive to materials, such as strand materials or flat substrates, used in the manufacture of nonwoven products. The nozzle includes a nozzle body having a liquid supply passage and a first liquid discharge orifice in fluid communication with the liquid supply passage. The first liquid discharge orifice extends along a first axis and is configured to discharge a first bead of the liquid adhesive. First and second pattern air discharge orifices in the nozzle body are associated with the first liquid discharge orifice. In addition, first and second cleaning and stabilizing air discharge orifices in the nozzle body are also associated with first liquid discharge orifice. The first and second pattern air discharge orifices and the first and second cleaning and stabilizing air discharge orifices are arranged around the first liquid discharge orifice at 90° alternating positions. That is, the first and second pattern discharge orifices are arranged 180° apart on opposite sides of the first liquid discharge orifice and the first and second cleaning and stabilizing air discharge orifices are arranged 180° apart on opposite sides of the first liquid discharge orifice at positions 90° from the first and second pattern air discharge orifices.

The two sets of air discharge orifices have different advantageous functions each in association with the corresponding liquid discharge orifice. The pattern air discharge orifices vacillate the first bead of adhesive back and forth in a vacillating plane containing the first and second pattern air discharge orifices. The first and second cleaning and stabilizing air discharge orifices emit jets of air in a direction parallel to the first axis to clear airborne contaminants, such as dust, away from the first liquid discharge orifice and to stabilize the first bead of adhesive in the vacillation plane. Thus, not only do the cleaning and stabilizing air discharge orifices clean the nozzle of contaminants, such as dust which may clog the liquid discharge orifice, they also help maintain the vacillating adhesive bead in a single plane, which is generally a plane perpendicular to the machine direction of the material. This ensures a more uniform adhesive bead pattern and, therefore, more accurate and consistent bead placement.

More specifically, the nozzle may comprise more than one liquid discharge orifice and associated sets of pattern air discharge orifices and cleaning and stabilizing air discharge orifices, depending on the application needs. Further, the nozzle is advantageously coupled to an on/off dispensing module including a valve mechanism for selectively allowing and preventing the flow of adhesive from the liquid discharge orifice or orifices. The first and second pattern air discharge orifices preferably converge toward the axis defining the associated liquid discharge orifice, while the first and second cleaning and stabilizing air discharge orifices are preferably parallel to the axis of the associated liquid discharge orifice. In addition, the liquid discharge orifice preferably opens on the apex of a projecting nozzle portion, while the first and second pattern air discharge orifices preferably open on the base of the projecting nozzle portion. The first and second cleaning and stabilizing air discharge orifices open on the apex as well, directly adjacent the associated liquid discharge orifice.

A method of applying an adhesive bead in accordance with the invention comprises moving a strand of material in a linear direction and positioning the liquid discharge orifice of the nozzle spaced apart from the strand of material. An adhesive bead is extruded from the liquid discharge orifice toward the strand of material and first and second pattern air jets are discharged from the nozzle to vacillate the adhesive bead back and forth in a vacillation plane while the vacillating adhesive bead attaches to the strand of material. Cleaning and stabilizing air jets are discharged from the first and second cleaning and stabilizing air jet orifices to clear airborne contaminants away from the liquid discharge orifice and to stabilize the vacillating bead of adhesive in the vacillation plane. In another aspect of the method, the first and second cleaning and stabilizing air jets are preferably directed at a lower pressure than the first and second pattern air jets. In addition, the first and second cleaning and stabilizing air jets may be discharged intermittently or continuously, while the first and second pattern air jets are preferably directed in a continuous manner to produce the vacillating pattern. The cleaning and stabilizing air jets may be continued after the adhesive bead extrusion has stopped to continue to clear away airborne contaminants from the liquid discharge orifice.

These and other objects, advantages and features of the invention will become more readily apparent to those of ordinary skill in the art upon review of the following detailed description taken in conjunction with the accompanying drawings.

DETAILED DESCRIPTION

Figure 2:
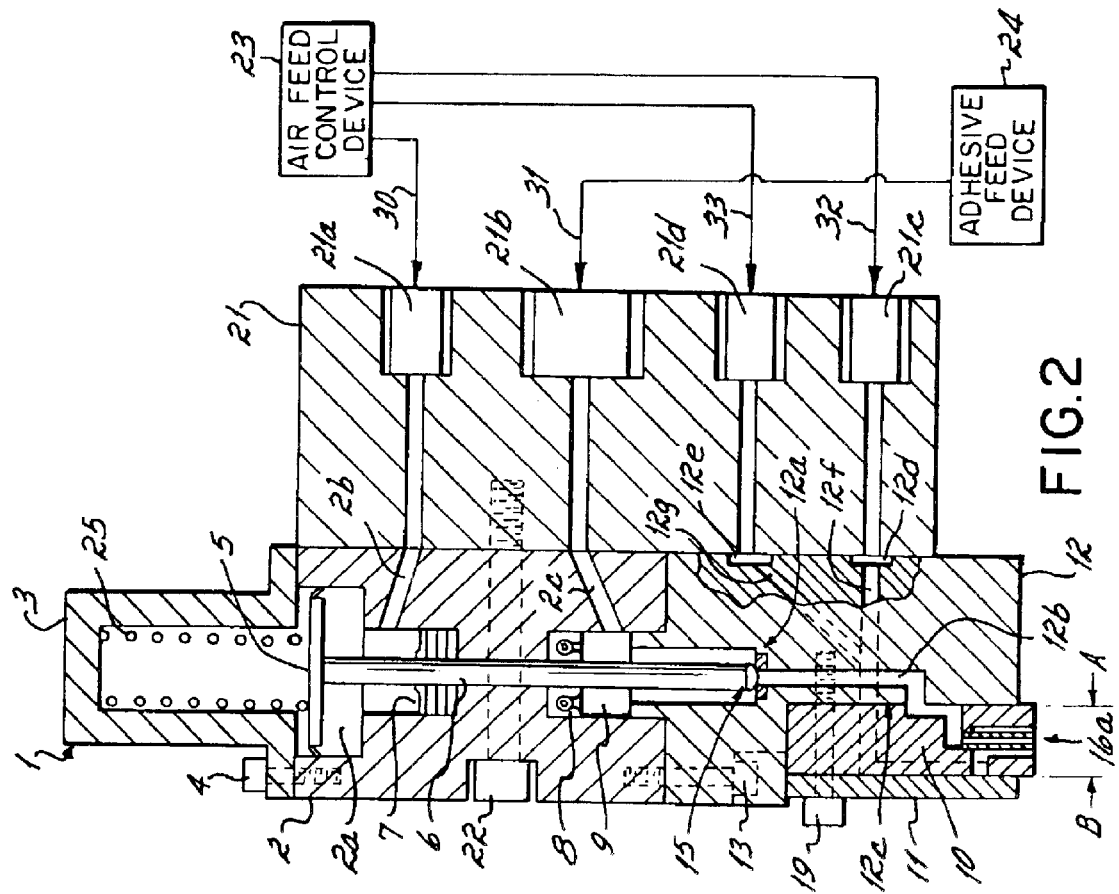
FIG. 2 is a vertical sectional view of a coating device according to the present invention.

The preferred embodiment of carrying out the present invention will now be described. First, an adhesive fed from a well-known adhesive feed device is extruded as a continuous bead from an adhesive discharge nozzle installed above a long strand of material traveling at high speed in noncontact with said material, by opening the valve mechanism of a coating device. Pattern air is jetted from two pattern air jet nozzles provided on both sides of the adhesive discharge nozzle onto the continuous adhesive beads extruded from the adhesive discharge nozzle, the pattern air comes into contact with the adhesive beads and causes the adhesive beads to begin an oscillating or vacillating motion. In this disclosure, the terms oscillating and vacillating are synonymous. This vacillating motion swings in the form of a wave centered around the adhesive discharge nozzle in the direction of the pattern air jet nozzles.

The oscillated adhesive beads are deposited on the surface of the strand material so as to straddle the traveling strand in the crossing direction. Accordingly, the position of the pattern air jet nozzles relative to the adhesive discharge nozzle must be located in the direction of crossing the traveling strand material. The adhesive thus deposited on the surface of the strand material begins a fluid movement as a viscous liquid after the deposition, and makes its way around the strand material by drooping to the underside. The bead also flattens out, so that the adhesive is applied all around the strand material so as to enwrap it.

The above operations are performed while jetting cleaning air intermittently or continuously from the cleaning air jets provided adjacent to the front side and rear side of the adhesive discharge nozzle, thereby enabling continuous operation. In other words, the problem of airborne fibrous particles adhering to the nozzle holes, piling up and solidifying with the passage of time is avoided. This can prevent destabilizing the coating process and obstructing the extrusion of the adhesive. Furthermore, when the cleaning air is jetted continuously, irregular swings of the adhesive can be prevented, and a rectifying or stabilizing effect such as to make the bead-form adhesive swing regularly in the right and left directions is achieved.

It is desirable to adjust the discharge pressure of the cleaning air to a pressure lower than the discharge pressure of the pattern air during the extrusion of the adhesive. However, the discharge pressure of the cleaning air can be raised while the valve mechanism is closed, i.e., the extrusion of the adhesive is stopped, and thereby the adhesion of dust is prevented more effectively.

The present invention will now be described in concrete terms with the use of figures which show an actual example of the present invention. Here, the present actual example uses a structure for applying an adhesive to three strand materials simultaneously with one coating device, but the present invention is not limited to this example.

Figure 1:
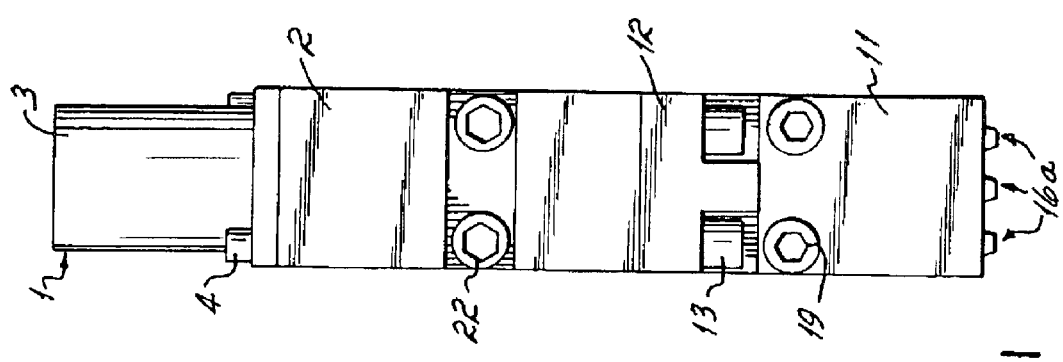
FIG. 1 is a front view of a coating device according to the present invention.
Figure 3:
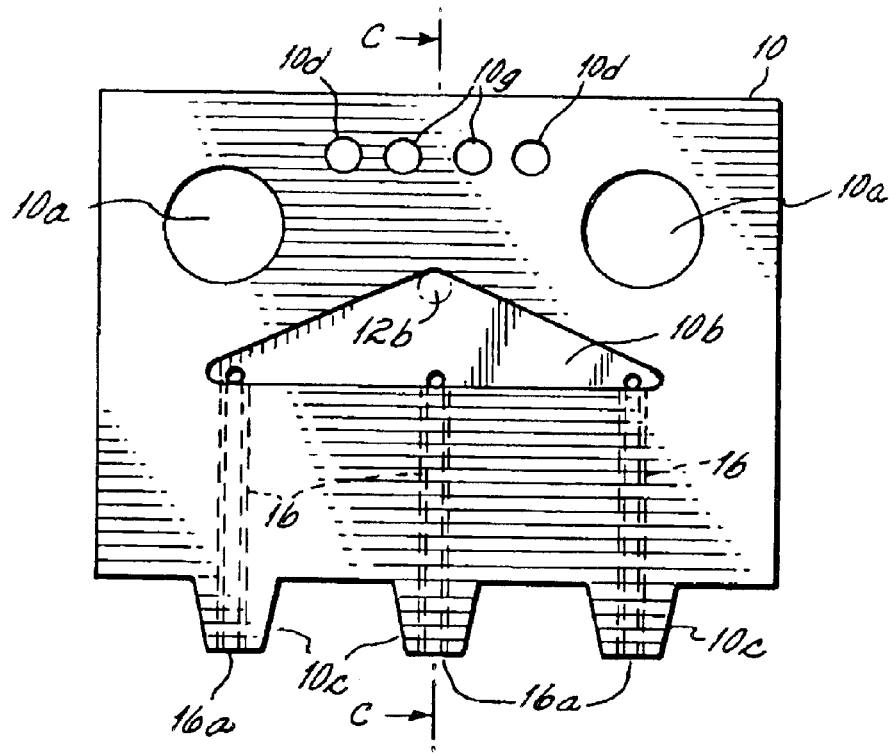
FIG. 3 is a diagram of the nozzle block seen from side A in FIG. 2.
Figure 4:
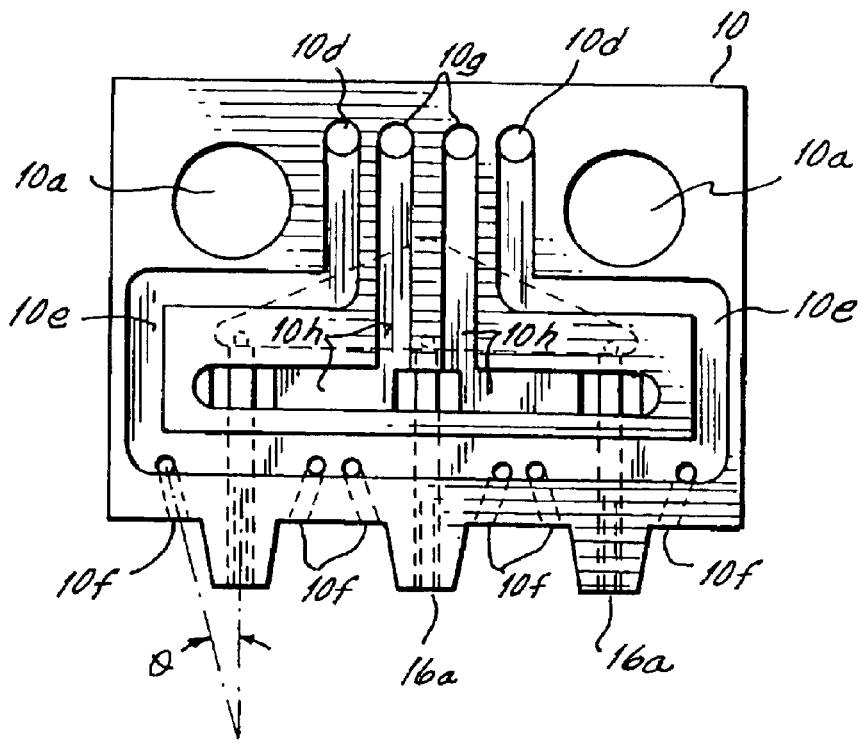
FIG. 4 is a diagram of the nozzle block seen from side B in FIG. 2.
Figure 5:
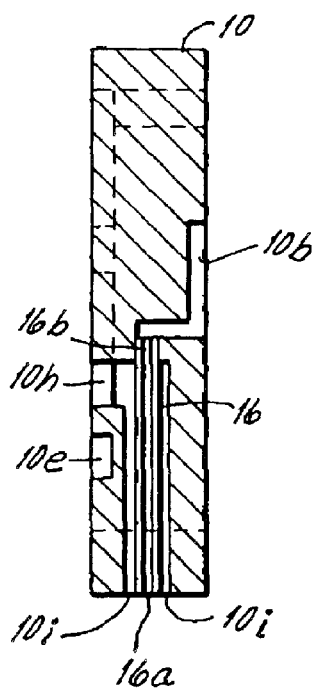
FIG. 5 is a sectional view along C—C of FIG. 3.
Figure 6:
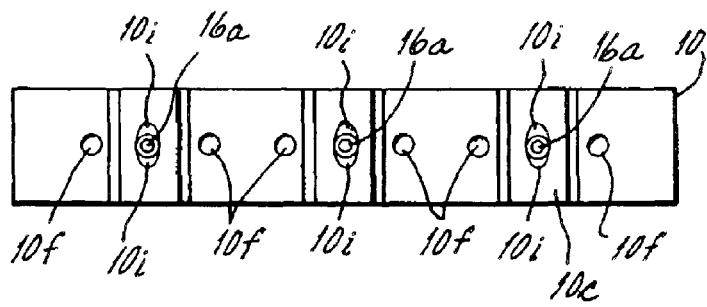
FIG. 6 is a base view of the nozzle block.

In FIGS. 1 and 2, the coating device 1 has a structure with a valve mechanism 15 which is opened and closed by operating air 30. Specifically, a gun body 2 forms the coating device 1, and a cylinder 2a is formed in the upper part of the gun body 2 and a piston 5 moves up and down and is located inside the cylinder 2a. A piston cover 3 is attached with a plurality of bolts 4 to the top of the gun body 2. A spring 25 forces the piston 5 downward at all times.

A valve stem 6 is fastened to the piston 5, and the valve stem 6 extends into a liquid chamber 9 through seal members 7 and 8 provided in a small-diameter section in the gun body 2. An adapter 12 is attached with a plurality of bolts 13 to the lower part of the gun body 2. A valve seat part 12a leading to the liquid chamber 9 and an adhesive through-hole 12b downstream from the valve seat part 12a are formed inside the adapter 12. The adhesive through-hole 12b is open to a flat section 12c of the adapter 12, with its lower part bent in an L-shape. The valve stem 6 and valve seat part 12a of the adapter 12 comprise the valve mechanism 15. The valve mechanism 15 is kept closed at all times by the force of the spring 25.

A nozzle block 10, and a nozzle holding plate 11 are stacked and attached with a plurality of bolts 19 to the flat section 12c of the adapter 12. The configuration of the nozzle block 10 is shown in detail in FIGS. 3–6. The nozzle block 10 is provided with attaching holes 10a for the bolts 19. A triangular groove 10b for an adhesive 31 is formed on side A, and three pipe-shaped nozzle members 16 communicating with the triangular groove 10b are provided so as to open to the triangular groove 10b by fixing a neck part 16b firmly in the nozzle block 10 by means such as pressure insertion, brazing, or welding. Furthermore, the nozzle member 16 opens its leading end as an adhesive discharge nozzle or orifice 16a to a protrusion 10c that protrudes on the underside of the nozzle block 10. The adhesive through-hole 12b of the adapter 12 opens to the top of the triangular groove 10b.

A through-hole 10d for pattern air 32 extends through the nozzle block 10. The through-holes 10d communicate with a pattern air groove 10e on side B of the nozzle block 10. The pattern air groove 10e communicates with pattern air jet nozzles or orifices 10f which open to both sides of each adhesive discharge nozzle or orifice 16a on the underside of the nozzle block 10. The pattern air nozzles 10f may be bored in the vertical direction, but good results can be obtained if they are bored so as to adjust the angle Θ to the adhesive discharge nozzle 16a in the range of 10–20 degrees. Furthermore, a through-hole 10g for cleaning air 33 extends through the nozzle block 10. The through-holes 10 communicate with a cleaning air groove 10h on side B of the nozzle block 10. The cleaning air groove 10h further communicates with cleaning and stabilizing air jet orifices 10i which are open in a crescent shape in front and behind the nozzle member 16.

The nozzle block 10 is stacked with the nozzle holding plate 11 and attached to the flat part 12c of the adapter 12. The triangular groove 10b provided on side A of the nozzle block 12 forms a space that is closed by the flat part 12c of the adapter 12, and functions as a path for the adhesive 31. The pattern air groove 10e and cleaning air groove 10h provided on side B form grooves closed by the nozzle holding plate 11, and function as a pattern air path and a cleaning air path, respectively.

An operating air through-hole 2b communicates with the cylinder 2a below the piston 5 and an adhesive through-hole 2c communicates with the liquid chamber 9. The gun body 2 is fastened together with the adapter 12 with a plurality of bolts 22 to a manifold 21. Furthermore, the adapter 12 is provided with a horizontally long groove 12d for pattern air 32 and a horizontally long groove 12e for cleaning air 33 on the side meeting the manifold 21. The horizontally long groove 12d is provided with two pattern air through-holes 12f that communicate with two through-holes 10d of the nozzle block 10. The horizontally long groove 12e is provided with two cleaning air through-holes 12g that communicate with two through-holes 10g of the nozzle block 10, though only one air through-hole is shown for each in FIG. 2.

The manifold 21 is provided with an operating air feed hole 21a that communicates with the operating air through-hole 2b and an adhesive feed hole 21b that communicates with the adhesive through-hole 2c. A pattern air feed hole 21c communicates with the horizontally long groove 12d and a cleaning air feed hole 21d communicates with the horizontally long groove 12e provided in the adapter 12. The operating air feed hole 21a, pattern air feed hole 21c, and cleaning air feed hole 21d are connected via a tubular path such as a hose to an air feed control device 23 equipped with the function to regulate the pressure, flow rate, and temperature of the air and the function of on and off control, these functions working independently for each amount of air. The adhesive feed hold 21b is connected via a tubular path such as a hose to an adhesive feed device 24 equipped again with the function to control pressure, flow rate, etc.

The action of the coating device 1 thus constructed will be explained below. First, the adhesive 31 fed from the adhesive feed device 24 is stored in the liquid chamber 9, after passing through the adhesive feed hole 21b of the manifold 21, and the adhesive through-hole 2c of the gun body 2. If the operating air 30 fed from the air feed control device 23 is fed into the cylinder 2a below the piston 5 via the operating air feed hole 21a of the manifold 21 and the operating air through-hole 2b of the gun body 2, the piston 5 and valve stem 6 move upward against the force of the spring 25, and the valve mechanism 15 is opened.

Figure 7:
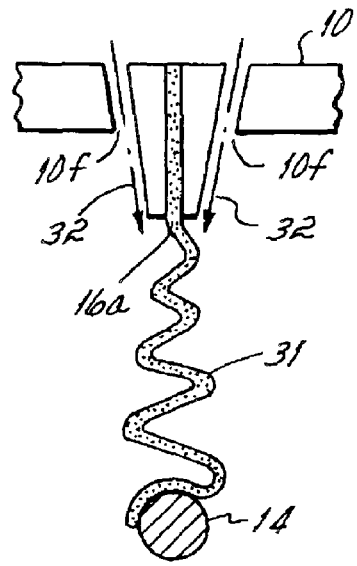
FIG. 7 is a schematic diagram which shows the manner of the adhesive being applied.

The adhesive 31 in the liquid chamber 9 is extruded in the form of continuous beads from the adhesive discharge nozzles 16a of the nozzle member 16 through the adhesive through-hole 12b of the adapter 12 and the triangular groove 10b of the nozzle block 10, while the valve mechanism 15 is open. Pattern air 32 fed from the air feed control device 23 is jetted from the pattern air jet nozzles 10f through the pattern air feed hole 21c of the manifold 21, the pattern air through-hole 12f of the adapter 12, and the through-holes 10d and pattern air groove 10e of the nozzle block 10. The bead-form adhesive 31 begins a swing motion from side to side in a vacillation plane under the influence of the pattern air 32 as shown in FIG. 7.

Figure 8:
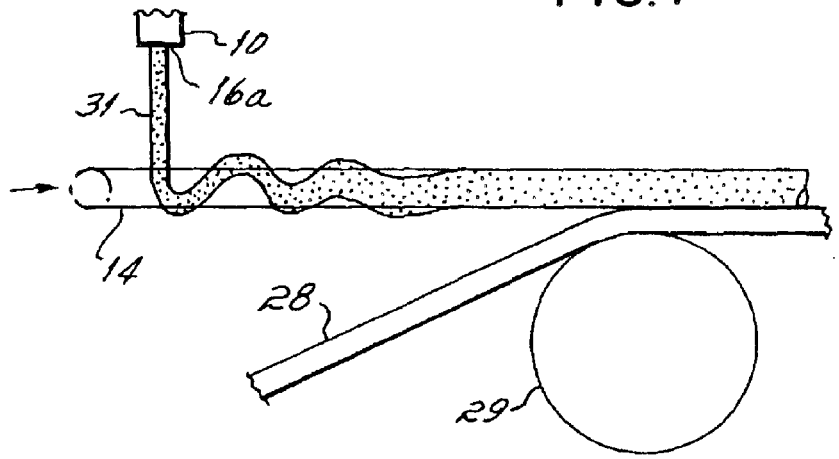
FIG. 8 is a schematic diagram which shows the manner of the adhesive being applied.
Figure 9:
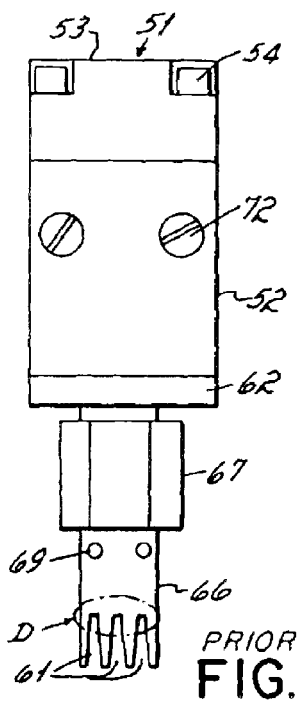
FIG. 9 is a front view of a conventional coating device.
Figure 10:
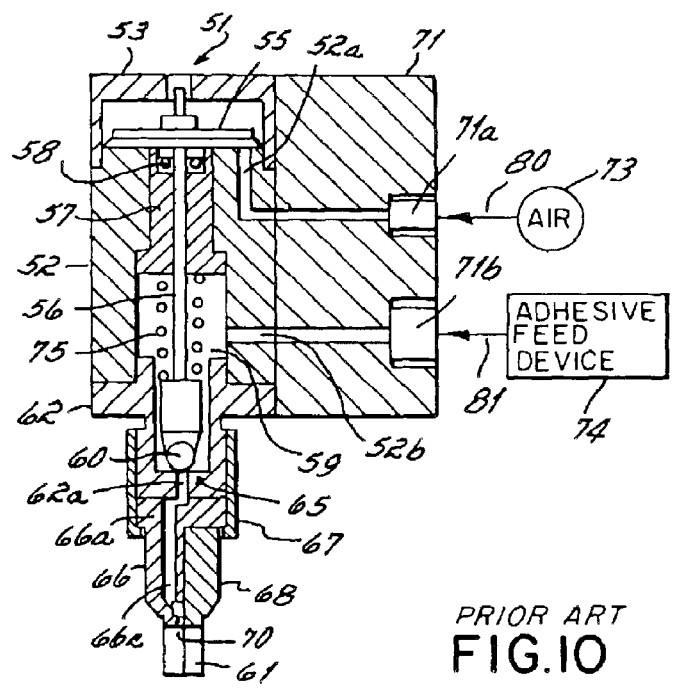
FIG. 10 is a vertical sectional view of a conventional coating device.
Figure 11:
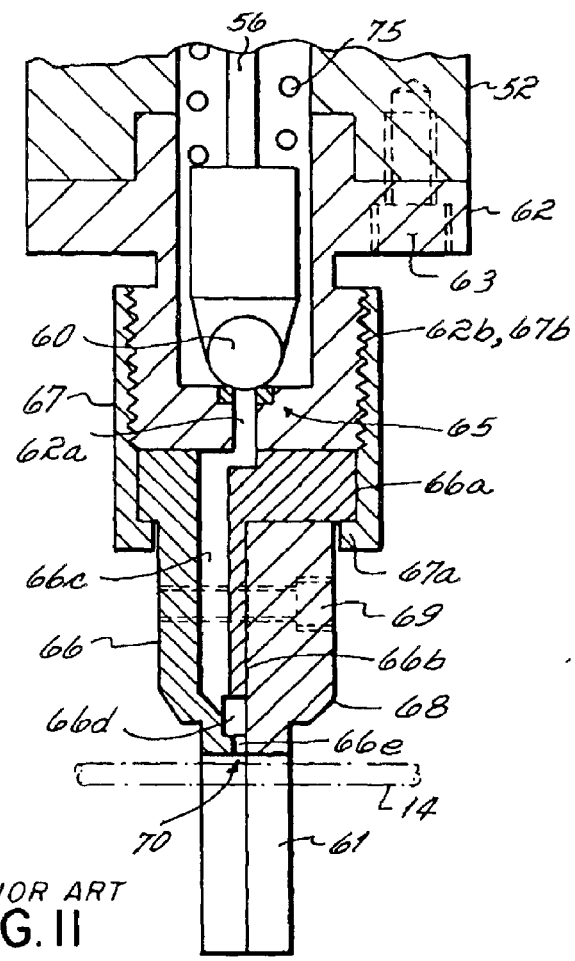
FIG. 11 is an expanded view of the leading end part of FIG. 10.
Figure 12:
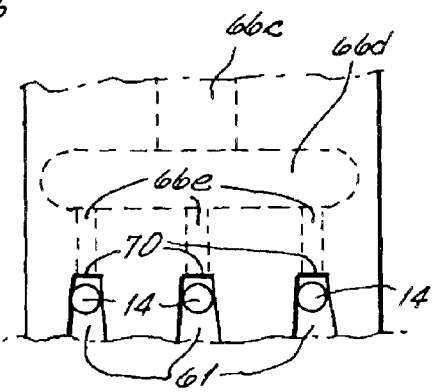
FIG. 12 is an expanded view of part D of FIG. 9.

The adhesive 31 is swung in the direction of crossing for the moving strand material 14 which is the material to be coated. The adhesive is applied to the surface of the strand material 14 so as to straddle the strand material 14 which is continuously transferred in noncontact below the adhesive discharge nozzle 16a. The adhesive 31 is deposited on the surface of the strand material 14 and begins a fluid movement as a viscous liquid after deposition, and makes its way to the underside of the strand material 14 and also flattens out to form a film, so that the adhesive is applied all around the strand material 14 so as to enwrap it as shown in FIG. 8. The strand material 14 coated with the adhesive is bonded further downstream with a substrate 28 on a roll 29.

These operations are performed while jetting cleaning air 33 from the cleaning and stabilizing air jet orifices 10i in crescent shaped orifices provided adjacent to the front side and rear side of the adhesive discharge nozzle 16a. The cleaning air 33 fed from the air feed control device 23 is jetted from the cleaning and stabilizing air jet orifices 10i through the cleaning air feed hole 21d of the manifold 21, the cleaning air through-hole 12g of the adapter 12, and the through-holes 10g and the cleaning air groove 10h of the nozzle block 10.

The jetting of cleaning air 33 prevents fine fibrous dust floating in the air from sticking around the adhesive discharge nozzles 16a, and enables stable application of the adhesive for long periods of time. This cleaning air jetting may be continuous or intermittent. If the cleaning air is jetted continuously, a rectifying effect such as to make the bead-form adhesive swing regularly in the right and left directions by preventing irregular swings of the adhesive is also achieved. Furthermore, it is desirable to adjust the discharge pressure of the cleaning air to a pressure lower than the discharge pressure of the pattern air. The discharge pressure of the cleaning air can be raised while the valve mechanism is closed, i.e., the extrusion of the adhesive is stopped, and thereby the adhesion of dust is prevented more effectively. Moreover, according to test results, it is desirable to adjust the distance H from the leading end of the adhesive discharge nozzle 16a to the strand material 14 to 5–20 millimeters.

To stop the discharge of the adhesive, the operating air 30 being fed to the underside of the piston 5 is released by the operation of the air feed control device 23, then the piston 5 and the valve stem 6 move downward by the force of the spring 25, and the valve mechanism 15 closes and the dis-charge of the adhesive stops. Thus, the open and shut operation of the valve mechanism 15 can achieve intermittent application of the adhesive.

TEST EXAMPLE

Many tests of applying an adhesive to a strand material were repeated under the following conditions, and good results were obtained in all the tests. The conditions were as follows:

(1) strand material used as the substrate: strand elastic, thickness 560 denier (diameter about 0.28 mm), traveling speed 150–170 m/minute.

(2) Type of adhesive used: product No. H-6830 from Nitta Findley Co., Ltd. and product No. HE-1 from Japan N.S.C. Co., Ltd., both being rubber-based hot-melt adhesives.

(3) Melting temperature of adhesive upon heating: 150° C. for H-6830 and 160° C. for HE-1.

(4) Distance from the leading end of the adhesive discharge nozzle to the workpiece: 5–20 mm.

(5) Diameter of the adhesive discharge nozzle: 0.6 mm.

(6) Discharge pressure of the adhesive: 7–14 $kg/cm^2$.

(7) Diameter of pattern air jet nozzle: two diameters, 0.46 mm and 0.50 mm.

(8) Pressure of pattern air: 0.3–1.0 $kg/cm^2$.

(9) Area of cleaning air jet: approximately equal to the opening area of the pattern air jet nozzle.

(10) Pressure of cleaning air: 0.1–0.8 $kg/cm^2$, continuous and intermittent jetting.

According to the device and method of the present invention of applying an adhesive to strand materials, the coating device is placed in noncontact with the strand materials, as described above, and thereby a device and a method for applying an adhesive to strand materials is provided. The generation of stretching stress in the strand materials or the severing of these materials as sometimes seen in contact application according to one known conventional technique can be avoided. No change is required in the device even if the thickness and shape of the strand material is changed. The all-around attachment of the adhesive is good. Moreover, high-quality coating of the adhesive can be achieved with clean nozzles with no adhesion of dust and with accurate, uniform placement of the adhesive.

While the present invention has been illustrated by a description of a preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims, wherein.

I claim:

1. A nozzle for dispensing a liquid adhesive to strand materials used in the manufacture of nonwoven products, comprising:

a nozzle body having a liquid supply passage and a first liquid discharge orifice in fluid communication with said liquid supply passage, said first liquid discharge orifice extending along a first axis and configured to discharge a first bead of the adhesive, first and second pattern air discharge orifices in said nozzle body and associated with said first liquid discharge orifice, said first and second pattern air discharge orifices arranged 180° apart on opposite sides of said first liquid discharge orifice and configured to direct pressurized pattern air at the first bead of adhesive discharged through said first liquid discharge orifice thereby vacillating the first bead of adhesive back and forth in a vacillation plane containing said first and second pattern air discharge orifices, and first and second cleaning and stabilizing air discharge orifices in said nozzle body and associated with said first liquid discharge orifice, said first and second cleaning and stabilizing air discharge orifices arranged 180° apart on opposite sides of said first liquid discharge orifice and positioned 90° from said first and second pattern air discharge orifices, said first and second cleaning and stabilizing air discharge orifices configured to direct pressurized cleaning and stabilizing air in a direction parallel to said first axis to clear airborne contaminants away from said first liquid discharge orifice and to stabilize the first bead of adhesive in said vacillation plane.

2. The nozzle of claim 1, wherein said nozzle body further comprises:

a second liquid discharge orifice in fluid communication with said liquid supply passage, said second liquid discharge orifice extending along a second axis and configured to discharge a second bead of the adhesive, third and fourth pattern air discharge orifices in said nozzle body and associated with said second liquid discharge orifice, said third and fourth pattern air discharge orifices arranged 180° apart on opposite sides of said second liquid discharge orifice and positioned in said vacillation plane, said third and fourth pattern air discharge orifices configured to direct pressurized pattern air at the second bead of adhesive discharged through said second liquid discharge orifice thereby vacillating the second bead of adhesive back and forth in said vacillation plane, and third and fourth cleaning and stabilizing air discharge orifices in said nozzle body and associated with said second liquid discharge orifice, said third and fourth pattern air discharge orifices arranged 180° apart on opposite sides of said second liquid discharge orifice and positioned 90° from said third and fourth pattern air discharge orifices, said third and fourth cleaning and stabilizing air discharge orifices configured to direct pressurized cleaning and stabilizing air in a direction parallel to said second axis to clear airborne contaminants away from the second liquid discharge orifice and to stabilize the second bead of adhesive in said vacillation plane.

3. The nozzle of claim 2, wherein said nozzle body further comprises:
   a third liquid discharge orifice in fluid communication with said liquid supply passage, said third liquid discharge orifice extending along a third axis and configured to discharge a third bead of the adhesive,
   fifth and sixth pattern air discharge orifices in said nozzle body and associated with said third liquid discharge orifice, said fifth and sixth pattern air discharge orifices arranged 180° apart on opposite sides of said third liquid discharge orifice and positioned in said vacillation plane, said fifth and sixth pattern air discharge orifices configured to direct pressurized pattern air at the third bead of adhesive discharged through said third liquid discharge orifice thereby vacillating the third bead of adhesive back and forth in said vacillation plane, and
   fifth and sixth cleaning and stabilizing air discharge orifices in said nozzle body and associated with said third liquid discharge orifice, said fifth and sixth pattern air discharge orifices arranged 180° apart on opposite sides of said third liquid discharge orifice and positioned 90° from said fifth and sixth pattern air discharge orifices, said fifth and sixth cleaning and stabilizing air discharge orifices configured to direct pressurized cleaning and stabilizing air in a direction parallel to said third axis to clear airborne contaminants away from said third liquid discharge orifice and to stabilize the third bead of adhesive in said vacillation plane.

4. The nozzle of claim 1, wherein said first and second pattern air discharge orifices converge toward said first axis.

5. The nozzle of claim 1, wherein said nozzle body further comprises a projecting nozzle portion having an apex and a base, said first liquid discharge orifice opening on said apex and said first and second pattern air discharge orifices opening on said base.

6. The nozzle of claim 5, wherein said first and second cleaning and stabilizing air discharge orifices open on said apex.

7. A device for dispensing a liquid adhesive to materials used in the manufacture of nonwoven products, comprising:
   a valve body including an adhesive input passage including a valve mechanism operative to selectively allow and prevent adhesive flow through said adhesive input passage,
   a nozzle body coupled to said valve body, said nozzle body having a liquid supply passage in fluid communication with said adhesive input passage to selectively receive the adhesive flow and a first liquid discharge orifice in fluid communication with said liquid supply passage, said first liquid discharge orifice extending along a first axis and configured to discharge a first bead of the adhesive,
   first and second pattern air discharge orifices in said nozzle body and associated with said first liquid discharge orifice, said first and second pattern air discharge orifices arranged 180° apart on opposite sides of said first liquid discharge orifice and configured to direct pressurized pattern air at the first bead of adhesive discharged through said first liquid discharge orifice thereby vacillating the first bead of adhesive back and forth in a vacillation plane containing the first and second pattern air discharge orifices, and
   first and second cleaning and stabilizing air discharge orifices in said nozzle body and associated with said first liquid discharge orifice, said first and second cleaning and stabilizing air discharge orifices arranged 180° apart on opposite sides of said first liquid discharge orifice and positioned 90° from said first and second pattern air discharge orifices, said first and second cleaning and stabilizing air discharge orifices configured to direct pressurized cleaning and stabilizing air in a direction parallel to said first axis to clear airborne contaminants away from said first liquid discharge orifice and to stabilize the first bead of adhesive in said vacillation plane.

8. The device of claim 7, wherein said nozzle body further comprises:
   a second liquid discharge orifice in fluid communication with said liquid supply passage, said second liquid discharge orifice extending along a second axis and configured to discharge a second bead of the adhesive,
   third and fourth pattern air discharge orifices in said nozzle body and associated with said second liquid discharge orifice, said third and fourth pattern air discharge orifices arranged 180° apart on opposite sides of said second liquid discharge orifice and positioned in said vacillation plane, said third and fourth pattern air discharge orifices configured to direct pressurized pattern air at the second bead of adhesive discharged through said second liquid discharge orifice thereby vacillating the second bead of adhesive back and forth in said vacillation plane, and
   third and fourth cleaning and stabilizing air discharge orifices in said nozzle body and associated with said second liquid discharge orifice, said third and fourth pattern air discharge orifices arranged 180° apart on opposite sides of said second liquid discharge orifice and positioned 90° from said third and fourth pattern air discharge orifices, said third and fourth cleaning and stabilizing air discharge orifices configured to direct pressurized cleaning and stabilizing air in a direction parallel to said second axis to clear airborne contaminants away from the second liquid discharge orifice and to stabilize the second bead of adhesive in said vacillation plane.

9. The device of claim 8, wherein said nozzle body further comprises:
   a third liquid discharge orifice in fluid communication with said liquid supply passage, said third liquid discharge orifice extending along a third axis and configured to discharge a third bead of the adhesive,
   fifth and sixth pattern air discharge orifices in said nozzle body and associated with said third liquid discharge orifice, said fifth and sixth pattern air discharge orifices arranged 180° apart on opposite sides of said third liquid discharge orifice and positioned in said vacillation plane, said fifth and sixth pattern air discharge orifices configured to direct pressurized pattern air at the third bead of adhesive discharged through said third liquid discharge orifice thereby vacillating the third bead of adhesive back and forth in said vacillation plane, and
   fifth and sixth cleaning and stabilizing air discharge orifices in said nozzle body and associated with said third liquid discharge orifice, said fifth and sixth pattern air discharge orifices arranged 180° apart on opposite sides of said third liquid discharge orifice and positioned 90° from said fifth and sixth pattern air discharge orifices, said fifth and sixth cleaning and stabilizing air discharge orifices configured to direct pressurized cleaning and stabilizing air in a direction parallel to said third axis to clear airborne contaminants away from said third liquid discharge orifice and to stabilize the third bead of adhesive in said vacillation plane.

10. The device of claim 7, wherein said first and second pattern air discharge orifices converge toward said first axis.

11. The device of claim 7, wherein said nozzle body further comprises a projecting nozzle portion having an apex and a base, said first liquid discharge orifice opening on said apex and said first and second pattern air discharge orifices opening on said base.

12. The device of claim 11, wherein said first and second cleaning and stabilizing air discharge orifices open on said apex.

* * * * *